(12) United States Patent
Radley

(10) Patent No.: US 6,781,060 B2
(45) Date of Patent: Aug. 24, 2004

(54) ELECTRICAL CONNECTOR, A CABLE SLEEVE, AND A METHOD FOR FABRICATING AN ELECTRICAL CONNECTION

(75) Inventor: Ian Radley, Glenmont, NY (US)

(73) Assignee: X-Ray Optical Systems Incorporated, Albany, NY (US)

( * ) Notice: Subject to any disclaimer, the term of this patent is extended or adjusted under 35 U.S.C. 154(b) by 0 days.

(21) Appl. No.: 10/206,531

(22) Filed: Jul. 26, 2002

(65) Prior Publication Data

US 2004/0016559 A1 Jan. 29, 2004

(51) Int. Cl.⁷ .................................................. H01R 4/00
(52) U.S. Cl. ..................................... 174/84 R; 439/936
(58) Field of Search .............................. 439/276, 936, 439/204, 874; 174/76, 77 R, 110, 74 R, 75 C, 78, 84 R, 80

(56) References Cited

U.S. PATENT DOCUMENTS

| | | | | |
|---|---|---|---|---|
| 3,673,305 A | * | 6/1972 | Mashikian et al. | 174/12 BH |
| 3,954,321 A | * | 5/1976 | Casper | 439/275 |
| 4,105,037 A | * | 8/1978 | Richter et al. | 607/37 |
| 4,326,096 A | * | 4/1982 | Leitmann | 174/84 R |
| 4,335,928 A | | 6/1982 | Barrett et al. | 339/94 |
| 4,964,148 A | * | 10/1990 | Klostermann et al. | 378/127 |
| 5,272,612 A | * | 12/1993 | Harada et al. | 363/8 |
| 5,358,419 A | * | 10/1994 | Pejsa et al. | 439/201 |
| 5,596,621 A | * | 1/1997 | Schwarz et al. | 378/130 |
| 5,682,412 A | * | 10/1997 | Skillicorn et al. | 378/98.6 |
| 5,876,229 A | * | 3/1999 | Negle | 439/281 |
| 5,947,758 A | | 9/1999 | Enck | 439/181 |
| 6,213,805 B1 | | 4/2001 | Jedlitschka et al. | 439/271 |
| 6,452,102 B1 | * | 9/2002 | DeForest et al. | 174/75 C |

OTHER PUBLICATIONS

Product Information, Information About Dow Corning Brand Silicone Encapsulants, Dow Corning, 2000, 2001.
Product Information, SYLGARD 184, Silicone Elastomer, Dow Corning, Ref. No. 10–1204A–01, Jun. 15, 1998, DC 3399 1997–2001.

* cited by examiner

Primary Examiner—William H. Mayo, III
(74) Attorney, Agent, or Firm—Heslin Rothenberg Farley & Mesiti P.C.; Kevin P. Radigan, Esq.

(57) ABSTRACT

An electrical connector for a cable, a sleeve for a cable, and a method for fabricating an electrical connection. The connector, sleeve, and the method can all used for high-voltage electrical devices, for example, x-ray generating devices. In particular, the invention may be used for high-voltage electrical devices fabricated with an encapsulant, for example, a silicone potting material. In one aspect of the invention, the connector provides a high-voltage electrical connection having an integral bond between the high-voltage cable and the encapsulant with little or no air gaps. The connector includes a high-voltage cable having a sheath made from a first material, for example, polyethylene, and a sleeve made from a second material, for example, a silicone-based material, that is compatible with the encapsulant. Other aspects of the invention include a method for fabricating the connector and the sleeve used in the connector.

35 Claims, 3 Drawing Sheets

ELECTRICAL CONNECTOR, A CABLE SLEEVE, AND A METHOD FOR FABRICATING AN ELECTRICAL CONNECTION

CROSS-REFERENCE TO RELATED APPLICATIONS

This application contains subject matter which is related to the subject matter of the following applications, which are assigned to the same assignee as this application. The applications listed below are hereby incorporated by reference in their entirety:

"X-RAY TUBE AND METHOD AND APPARATUS FOR ANALYZING FLUID STREAMS USING X-RAYS" by Radley, U.S. Ser. No. 60/336,584 filed Dec. 4, 2001;

"A METHOD AND APPARATUS FOR DIRECTING X-RAYS" by Radley, U.S. Ser. No. 60/383,990 filed May 29, 2002;

"X-RAY SOURCE ASSEMBLY HAVING ENHANCED OUTPUT STABILITY" by Radley, et al., U.S. Ser. No. 60/398,965 filed Jul. 26, 2002; and "DIAGNOSING SYSTEM FOR AN X-RAY SOURCE ASSEMBLY" by Radley, U.S. Ser. No. 60/398,968 filed Jul. 26, 2002; and "METHOD AND DEVICE FOR COOLING AND ELECTRICALLY-INSULATING A HIGH VOLTAGE, HEAT-GENERATING COMPONENT" by Radley, et al., U.S. Ser. No. 60/398,966 filed Jul. 26, 2002.

TECHNICAL FIELD

This invention relates generally to high-voltage electrical connections and to methods for fabricating such connections. More particularly, the present invention provides improved high-voltage electrical connections for high-voltage electrical devices, such as x-ray tube assemblies which are assembled using encapsulants, and methods for making such high-voltage connections.

BACKGROUND OF THE INVENTION

High-voltage electrical devices, for example, devices operating at +/−10 kilovolts (kV) AC or DC or above, are common to many industries, for example, the power industry, the materials industry, and the analytical industry, among others. For example, x-ray producing devices, which are valuable tools used in a wide variety of industrial and medical applications, often operate with at least one component at high voltage, for example, at 50 kV or higher. X-ray producing devices are commonly used in areas such as diagnostic and therapeutic radiology, and materials testing, among others.

High-voltage devices may be fabricated with some form of encapsulation material, also known as an encapsulant, which provides a electrically insulating barrier around one or more components of a high-voltage device. Encapsulants may also minimize or exclude the presence of air about a high-voltage device, and thus minimize the potential for undesirable arcing and corona discharge to occur, may act as barriers to environmental contaminants, and may isolate components from shock or vibration loading. One encapsulant typically used in such devices is referred to in the art as a "potting material". Potting materials are typically flexible, elastomeric materials, such as silicone-based material, that can be molded (that is, "potted") about one or more components of a high-voltage device. Though conventional potting materials provide electrical insulation, their chemistry is sometimes incompatible with the sheathing on electrical cables that are often used to connect the high-voltage device to, for example, a high-voltage power source.

Encapsulants may be curable encapsulants. Curable encapsulants may be provided in a liquid or semi-liquid form which is curable to a solid or semi-solid under certain curing conditions.

Typically, high-voltage devices require at least one electrical connection to a high-voltage power source, often by means of a specially-designed high-voltage cable. Typically, these high-voltage cables are constructed with layers of insulating materials, such as a sheathing made of silicone, polyethylene, or other insulating materials. Silicone-sheathed high-voltage cables are very flexible and their silicone sheathing is typically compatible with silicone potting materials, that is, a satisfactory bond can be established between the silicone sheathing and the silicone potting materials during fabrication. Direct bonding of the silicone sheathing of the cable to the potting material can provide a contiguous bonded connection which, most importantly, can minimize or prevent the formation of any undesirable air gaps between the sheathing and potting material.

In high-voltage electrical connections air gaps must be minimized or avoided entirely. The presence of any air gaps in high-voltage electrical connections introduces the potential for high-voltage electrical arcing or corona discharge at the interface of the cable and the high-voltage device. High-voltage arcing can reduce the power and voltage transferred to the high-voltage device, can damage the connection or high-voltage device, can provide an undesirable fire risk, or provide a safety risk due to electric shock. High-voltage corona discharge can attack insulation materials and cause the insulation materials to degrade. However, though high-voltage silicone-sheathed cables are less susceptible to the formation of air gaps, silicone-sheathed cables are very expensive. Furthermore, silicone-sheathed cables are difficult to adapt for use with a variety of standard power supplies, such as power supplies with air gap connectors. Other more cost-effective and readily adaptable high-voltage cables, such as polyethylene-sheathed cables, are readily available; however, the sheathing of such cable, for example, polyethylene sheathing, is extremely difficult to bond directly to most encapsulants, for example, extremely difficult to bond to an uncured encapsulant. Most notably, polyethylene sheathing does not bond to uncured silicone-type potting materials. Conventionally, the use of polyethylene-sheathed high-voltage cables with silicone-based potting materials typically is hindered due to the incompatibility of the two materials and the use of such materials is prone to the formation of undesirable air gaps and consequent arcing or corona discharge in the high-voltage connection.

Thus, there is a need in the art to provide a method and device for using a cost-effective and readily adaptable high-voltage cable, for example, a polyethylene-sheathed cable, to form an electrical connection between a encapsulated high-voltage device, for example, an silicone-encapsulated high-voltage device, and a high-voltage power source. There is also a need in the art for a method for bonding of high-voltage cable, for example, a high power polyethylene-sheathed cable, to a high-power encapsulated device, for example, a high power silicone-encapsulated device, that minimizes or prevents the formation of air gaps and provides a contiguous bonded connection.

SUMMARY OF THE INVENTION

The present invention provides methods and apparatus which address many of the limitations of prior art methods and apparatus.

One aspect of the invention is an electrical connector for an electrical device. In this aspect of the invention, the device includes a conducting element at least partially encased in a curable encapsulant and the electrical connector includes a cable having a conductor and a sheath surrounding the conductor, the sheath comprising a first material that is not bondable with the uncured encapsulant; and a sleeve mounted to the sheath, the sleeve comprising a second material that is bondable with the uncured encapsulant; wherein the sleeve and the encapsulant form an essentially air-tight connection between the sleeve and the encapsulant when the encapsulant is cured. In one aspect of the invention, the electrical device comprises a high-voltage electrical device, for example, an x-ray tube, an x-ray transformer, a high-voltage rectifier, high-voltage power supply, or microwave generator, among other devices. In one aspect of the invention, the sleeve is mounted to the sheath by means of an adhesive, for example, an epoxy resin adhesive. In another aspect of the invention, the encapsulant is silicone encapsulant. In one aspect of the invention, the first material is a dielectric material, for example, a polyethylene dielectric material. In one aspect of the invention, the second material comprises a silicone material, for example, a cured silicone encapsulant.

Another aspect of the invention is a sleeve for a cable for use in connecting the cable to a device, for example, a high voltage device, such as a an x-ray tube, an x-ray transformer, a high-voltage rectifier, high-voltage power supply, or microwave generator, among other devices. In this aspect of the invention, the device includes a conducting element at least partially encased in a curable encapsulant and the cable includes a conductor and a sheath surrounding the conductor. The sheath is made of a first material that is not bondable with the uncured encapsulant. The sleeve may be a cylindrical tube made of a second material which is bondable with the uncured encapsulant to provide an essentially air-tight connection between the sleeve and the encapsulant when the encapsulant is cured. In one aspect of the invention, the curable encapsulant comprises a silicone encapsulant. In one aspect of the invention, the second material comprises a cured encapsulant. In another aspect of the invention, the sleeve may include an end cap, for example, an endcap having a hole through which the cable conductor can pass.

Another aspect of the invention is a method for fabricating an electrical connection for a device, for example, a high-voltage device, such as an x-ray tube, an x-ray transformer, a high-voltage rectifier, high-voltage power supply, or microwave generator, among other devices. The device may include a conducting element at least partially encased in a curable encapsulant. The method of the present invention includes providing a cable having a conductor and a sheath surrounding the conductor, the sheath having an outside surface having an outside diameter and comprising a first material that is not bondable with the uncured encapsulant; providing a cylindrical sleeve having an inside diameter about equal to the outside diameter of the sheath and comprising a second material that is bondable with the uncured encapsulant; mounting the sleeve on the sheath to provide a sleeved cable; attaching the conductor of the sleeved cable to the conducting element of the device; and at least partially encasing the conducting element and the sleeved cable in an encapsulant wherein the sleeve and encapsulant bond to provide an essentially air tight connection between the sleeve and the encapsulant. The mounting step may include abrading the outside surface of the sheath or applying an adhesive to the outside surface of the sheath. The method may also include applying an adhesive to the outside surface of the sheath, for example, applying an epoxy resin to the outside surface of the sheath. In one aspect of the invention, attaching the conductor of the sleeved cable to the conducting element may be practiced by soldering, brazing, or welding the conductor to the conducting element. In another aspect of the invention, the conductor and conducting element may be attached by means of an adhesive, for example, an electrically-conductive adhesive, for instance Tiga Silver 901 electrically-conductive adhesive sold by Resin Technology of South Easton, Mass., or its equivalent. In one aspect of the invention, the step of at least partially encasing the conducting element and the sleeved cable in an encapsulant may be practiced by at least partially encasing the conducting element and the sleeved cable in an encapsulant or potting material, for example, a silicone potting material.

These and other embodiments and aspects of the present invention will become more apparent upon review of the attached drawings, description below, and

BRIEF DESCRIPTION OF THE DRAWINGS

The subject matter which is regarded as the invention is particularly pointed out and distinctly claimed in the concluding portion of the specification. The invention, however, both as to organization and method of practice, together with further objects and advantages thereof, may best be understood by reference to the following detailed descriptions of embodiments of one or more aspects of the invention and the accompanying drawings in which:

DETAILED DESCRIPTION OF THE PREFERRED EMBODIMENTS

Figure 1:
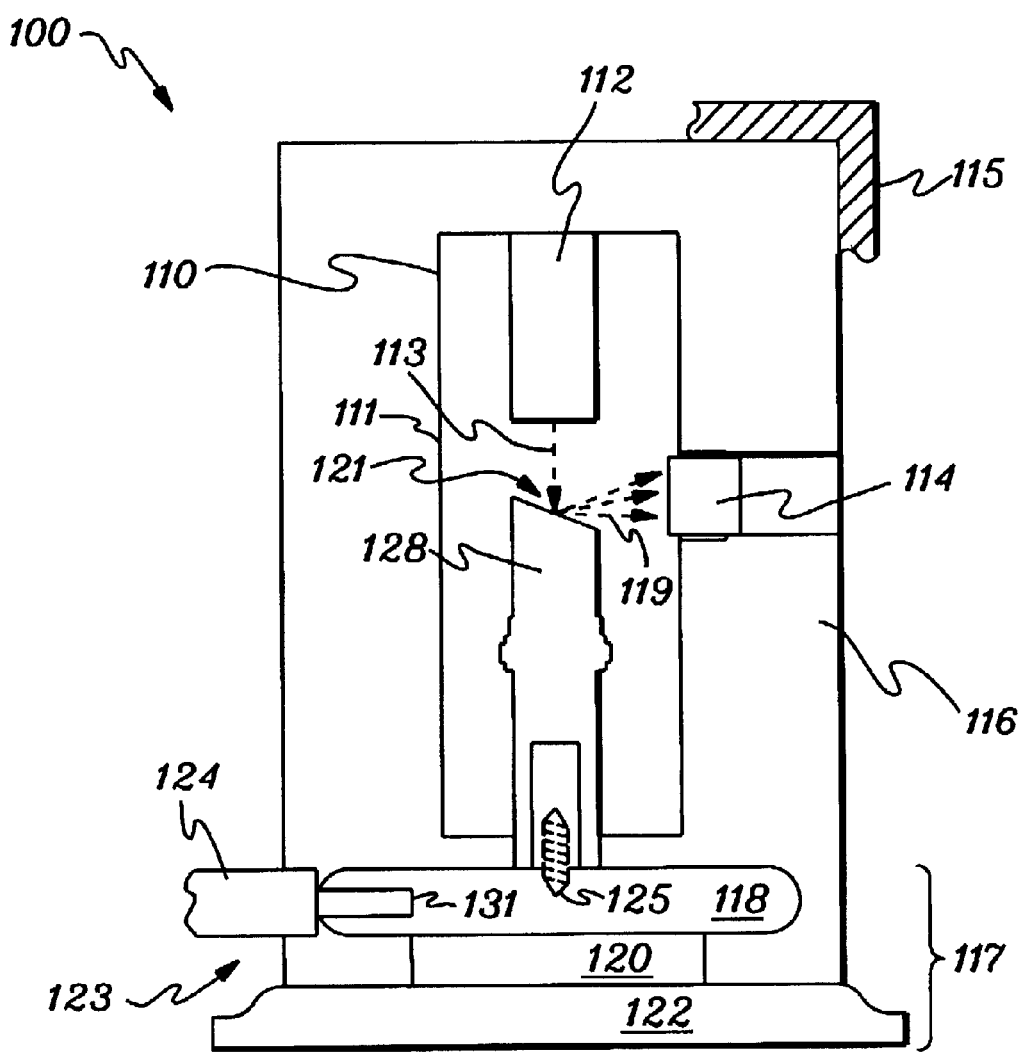
FIG. 1 illustrates a cross-sectional elevation view of a x-ray producing device having a conductive base to which electrical power is provided by means of a high-voltage cable connection according to one aspect of the present invention.

FIG. 1 illustrates a cross-sectional elevation view of an x-ray source assembly 100 having a conductive base 117 to which electrical power is provided by means of a high-voltage cable connection 123 according to one aspect of the present invention. Though the following description will describe aspects of the invention as they relate to high-voltage devices, it will be apparent to those of skill in the art that one or more aspects of the present invention may be used for devices that operate at voltages ranging from +/−5 kV to about +/−200 kV, for example, aspects of the invention may be used for devices that operate at less than 50 kV or at more conventional lower voltages. Though aspects of the invention will be described below with respect to providing high voltage into a component, the present invention may also be used to take power out of a component.

In the aspect of the invention shown in FIG. 1, x-ray source assembly 100 includes an x-ray tube 110, having a housing 111, an electron gun 112, an anode 128, and an x-ray transmission window 114; and a base assembly 117, having at least one conducting element 118, for example, an electrically-conducting material of any appropriate shape or size (such as, a conducting metal plate), connected to at least one high-voltage cable 124 via cable connection 123. The components of x-ray source assembly 100 typically are housed in an x-ray impermeable container 115 which is represented by a partial illustration in FIG. 1. As is conventional in the art, x-ray tube 110 and base assembly 117 may be surrounded and insulated by an encapsulant 116, for example, a moldable insulating material, such as a silicone-based potting material.

Enclosure 111 of x-ray tube 110 is typically a vacuum-tight enclosure typically formed of glass or ceramic. As is typical in the art, electron gun 112 is located opposite high-voltage anode 128, for example, having a voltage of about 50 kV or higher. Electron gun 112 is a device that, due to an applied voltage, emits electrons in the form of an electron stream, that is, an electron beam (e-beam) 113 as is well known in the art. High-voltage anode 128 provides a target upon which the electron stream impinges and as a result produces x-ray radiation 119, that is, x-rays, as is also well-known in the art. The impingement of electron beam 113 on anode 128 and the generation of x-rays 119 generates heat, typically a lot of heat. According to one aspect of the invention the heat generated in anode 128 is dissipated through base assembly 117. Anode 128 is typically electrically insulated from the body of x-ray tube 110 and electron gun 112. Encapsulant 116, for example, a silicone-based material, surrounds x-ray tube 110 (and may at least partially surround base assembly 117) and may aid in transferring generated heat away from anode 128 to, for example, base assembly 117.

Electron gun 112 is typically held at ground potential (for example, about zero volts) and high-voltage anode 128 is typically operated at a high-voltage potential, typically, at about 50 kv or above. As a result, the e-beam 113, which is emitting from electron gun 112 at ground potential is electrically attracted to the surface of HV anode 128, thereby producing x-rays 119. E-beam 113 impinges anode 128 and X-rays 119 are emitted from anode 128 from a location on anode 128 referred to as the "focal spot" 121 of the x-rays 119. The angle of orientation of the surface of anode 128 at focal spot 121 allows X-rays 119 to be directed toward transmission window 114. In contrast to container 115, transmission window 114 is typically formed from an x-ray transmissive material, such as beryllium (Be) and the like, which allows x-rays 119 to exit x-ray beam assembly 100, while maintaining the vacuum within x-ray tube 110.

As shown in FIG. 1, according to one aspect of the invention, the end of high-voltage anode 128 opposite the impingement surface protrudes through the body of x-ray tube 110 and is mechanically and electrically connected to base assembly 117, for example, by means of threaded mounting stud 125, for example, a thermally and electrically conducting mounting stud. According to one aspect of the invention, base assembly 117 may be any structure that at least provides a thermal and electrical path for conducting heat away from anode 128 while providing at least one high-voltage connection 123 to cable 124, for example, base assembly 118 may comprise one or more single metal plates 118. Plate 118 is typically made from a high electrically conductive and highly thermally-conductive material such as a copper-containing material, for example, copper; an aluminum-containing material; an iron-containing material, such as steel; a silver-containing material, or a gold-containing material, or a combination of two or more of these materials. However, according to one aspect of the invention, base assembly 117 comprises a multi-plate structure, for example, a three-plate structure that includes a first plate 118 made from a thermally conductive material, a second plate 120 made from a dielectric material, and third plate, or base plate, 122 made from a thermally-conductive material. A detailed description of a multi-plate base assembly 117 that can be used according to one aspect of the invention is disclosed in copending application "METHOD AND DEVICE FOR COOLING AND ELECTRICALLY-INSULATION A HIGH-VOLTAGE, HEAT-GENERATING COMPONENT Ser. No. 60/398,968 filed on filed on Jul. 26, 2002. The disclosure of this copending application is included by reference herein in its entirety.

Figure 1A:
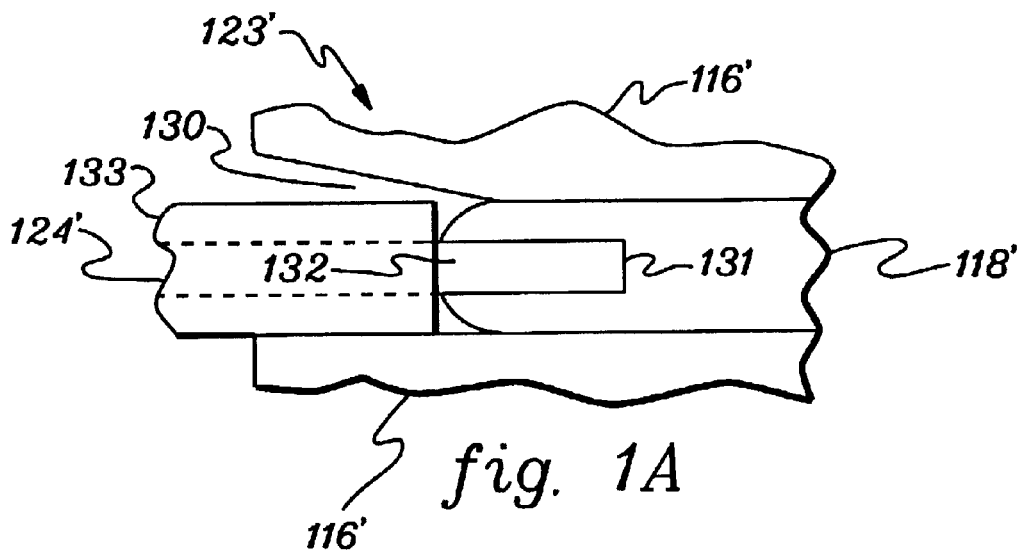
FIG. 1A is a detailed view of the high-voltage electrical connection shown in FIG. 1.

As illustrated in FIG. 1, according to one aspect of the invention, base assembly 117, comprises at least one connection 123 for connecting high-voltage cable 124 to base assembly 117. For example, connection 123 may include a blind hole 131 in plate 118 which provides a bonding cavity for cable 124. FIG. 1A illustrates a detailed view of connection 123' used by the inventor to attach a high-voltage cable 124' to a conductor plate 118' of a high-voltage device, for example, an x-ray tube. As shown in FIG. 1A, conductor plate 118' includes a blind hole 131, and high-voltage cable 124' includes a conductor 132 and a polyethylene-based sheath 133. In the arrangement shown, conductor plate 118', cable 124', and the high-voltage device (not shown) are encased in a curable silicone-based encapsulant 116'. As is conventional, conductor 132 is sized to be inserted into blind hole 131 and is then is soldered or otherwise retained in blind hole 131.

However, in the trials performed by the inventor, as shown in the arrangement in FIG. 1A, according to the conventional art of attaching a high-voltage cable 124' to conductor plate 118', the material of sheath 133 may be incompatible with curable encapsulant 116'. For example, as discussed above, the polyethylene-based sheath 133 on cable 124' is incompatible with (that is, is difficult to bond to) the uncured silicone-based encapsulant 116'. As a result, as the inventor found, after encapsulant 116' cures, sheath 133 may separate from cured encapsulant 116', for example, due to bending, shifting, or differences in thermal expansion, wherein one or more air gaps 130 may form around the circumference of sheath 133 of high-voltage cable 124'. As discussed above, the presence of air gaps 130 in a high-voltage connection may eventually cause degradation or electrical breakdown in the connection, and possibly failure of the high-voltage device or a fire or shock hazard. One or more aspects of the present invention provide a high-voltage connection to a high-voltage device with improved integrity between the cured encapsulant and the cable sheath wherein the presence of air gaps is minimized or eliminated.

Figure 2A:
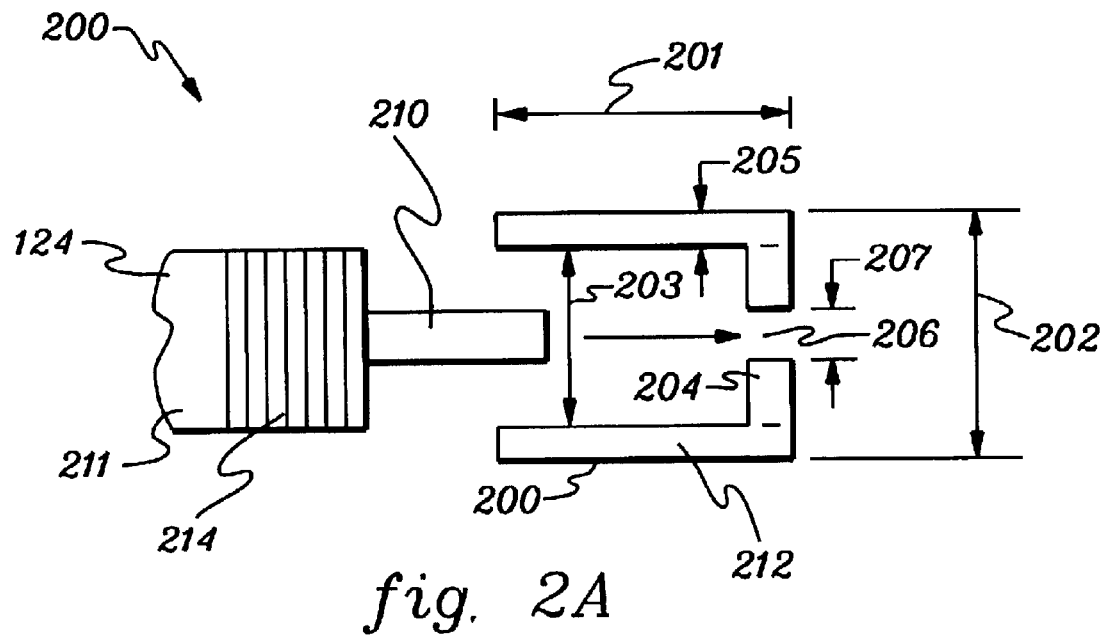
FIGS. 2A and 2B illustrate cross-sectional views depicting one method of fabricating a high-voltage connection according to one aspect of the present invention.
Figure 2B:
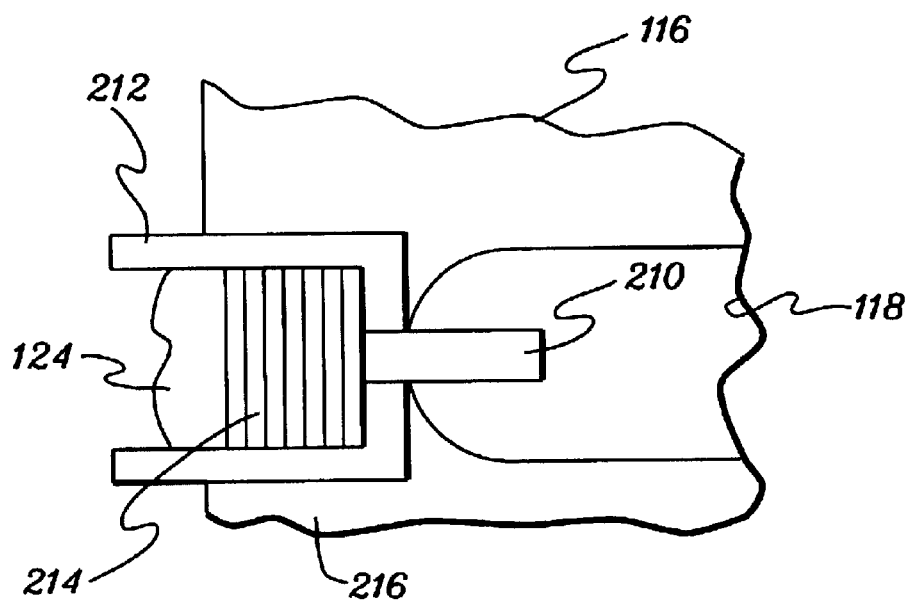

FIGS. 2A and 2B illustrate one embodiment of a high-voltage connection 200 of the present invention that, among other things, minimizes or even eliminates the presence of air gaps in high-voltage electrical connections. FIG. 2A illustrates a cross-sectional view of one method of fabricating an electrical connection according to one aspect of the invention. FIG. 2B illustrates a cross-sectional view of one aspect of the invention as assembled into a high-voltage device, for example, as assembled into base assembly 117 of x-ray producing device 100 shown in FIG. 1.

According to the aspect of the invention shown in FIG. 2A, the end of high-voltage cable 124, having a conductor 210 and an insulating sheath 211, for example, a polyethylene sheath, is inserted into a sleeve (or boot) 212. According to the present invention, sleeve 212 comprises a material that is compatible with (that is, will readily bond to, for example, without the need for an adhesive) encapsulant 116. In one aspect of the invention, sleeve 212 comprises a material which facilitates bonding of sleeve 212 with encapsulant 116. For example, in one aspect of the invention, encapsulant 116 is a silicone-based material, sheath 211 is a polyethylene-type material, and sleeve 212 comprises a silicone-based material which is compatible with encapsulant 116. In another aspect of the invention, encapsulant 116 and sleeve 212 comprise the same material, that is, sleeve 212 is made from cured encapsulant 116. In one aspect of the invention, an adhesive 214 may be applied to the outer surface of sheath 211 or to the inner surface of sleeve 212. According to one aspect of the invention, adhesive 214 may be an epoxy resin, for example, an epoxy resin sold under the name BONDiT™ by Reltek, LLC of Santa Rosa, Calif., for example, BONDiT™ B-45TH epoxy resin, but other suitable adhesives may be used depending, among other things, upon the material of sheath 211 and encapsulant 116. Epoxy resins, for example, BONDiT epoxy resins, typically cannot bond with uncured encapsulants. The chemistry of such resins, for example, their nitrogen content, interferes with the curing process of curable encapsulants. As a consequence, epoxy resins typically cannot be used to bond to curable encapsulants before the encapsulants are cured, specifically, epoxy resins typically cannot be used to bond cable sheaths to curable encapsulants before the encapsulants are cured.

In one aspect of the invention, encapsulant 116 may be a silicone-based encapsulant, for example, a silicone elastomeric encapsulant, for instance, a silicone-based elastomeric encapsulant marketed under the name SYLGARD® by Dow Chemical and described in Dow Chemical Product Information Sheet entitled "Information About Dow Chemical® Brand Silicone Encapsulants", 2001 (the disclosure of which is included by reference herein), though other encapsulants having comparable properties may be used. In one aspect of the invention, the material used for encapsulant 116 is Dow Chemical's Sylgard® 184 silicone elastomer, the properties of which are provided in Dow Chemical Product Information Sheet entitled "SYLGARD® 184 Silicone Elastomer", 2001, (the disclosure of which is included by reference herein).

In one aspect of the invention, high-voltage cable 124 may be an RG-8U-type polyethylene-sheathed cable having a copper center conductor 210, a polyethylene dielectric sheath 211, and a copper braided shield (not shown), though other types of high-voltage or low voltage cables may be used in other aspects of the present invention.

According to the aspect of the invention shown in FIGS. 2A and 2B, sleeve 212 comprises a cup-like structure having a side wall 200 and a base, or end cap, 204. According to one aspect of the invention, sleeve 212 comprises a cylindrical tube having side wall 200 but no base 204. Sleeve 212 includes a length 201, an outside diameter 202, and an inside diameter 203. The side wall 200 and base 204 may comprise a thickness 205. The base 204 typically includes a through hole 206 having a diameter 207 for passing conductor 210 through base 204. The dimensions of sleeve 212 will typically vary depending upon the size of cable 124 and conductor 210. However, typical dimensions of sleeve 212 include:

Length, 201: about 0.5 inches to about 6.0 inches, typically, about 1.0 inches Outside diameter, 202: about 0.25 inches to about 1.0 inch, typically, about 0.5 inches Inside diameter, 203: about 0.20 inches to about 1.0 inch, typically, about 0.45 inches Wall thickness, 205: about 0.01 inches to about 0.25 inches, typically, about 0.025 in. Hole diameter, 206: about 0.05 inches to about 0.25 inches, typically, about 0.1 inches.

According to one aspect of the invention, sleeve 212 may be cast from a material which is compatible with encapsulant 116, for example, cast in a conventional mold. For example, in one aspect of the invention, sleeve 212 may be cast from elastomer material in a conventional reusable mold. In another aspect of the invention, sleeve 212 may be cast from a curable encapsulant that is similar or identical to encapsulant 116, for example, sleeve 212 may be cast by curing an curable encapsulant, for example, a Dow Chemical SYLGARD® silicone elastomeric encapsulant, for instance, SYLGARD 184 silicone encapsulant, or its equivalent or derivative.

In another aspect of the invention, sleeve 212 may be fabricated from tape, for example, fabricated from tape containing silicone, for instance, a silicone tape. In another aspect of the invention, sleeve 212 may be fabricated from a heat shrinkable material, for example, a silicon-containing heat shrinkable material, for instance, a silicon heat shrinkable material sold under the name Fit Flex by Alpha Wire Company and adhering to UL Standard 224, or its equivalent.

Figure 3:
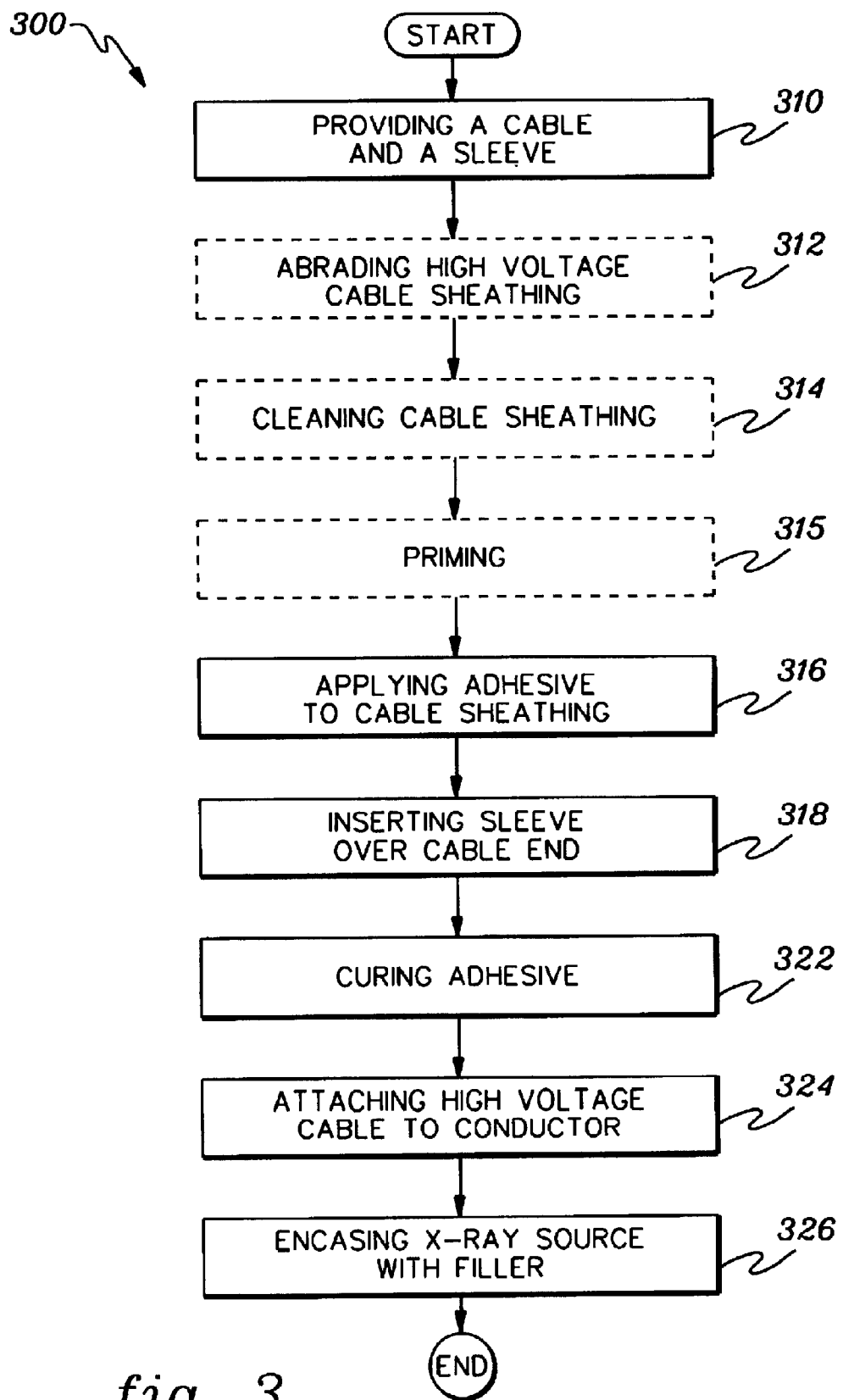
FIG. 3 is a flowchart of one embodiment of a method of fabricating a high-voltage connection according to one aspect of the present invention.

Another aspect of the present invention comprises a method for assembling a cable to a device, for example, a high-voltage cable to a high-voltage device, having an encapsulant 116, for example, a potting material or the like. According to this aspect of the invention, with reference to FIGS. 2A and 2B, a method 300 of assembling is illustrated in FIG. 3 and comprises the following steps. First, as indicted by 310 in FIG. 3, providing a cable with an exposed conductor 210 and providing a sleeve 212 fabricated from a material which is compatible with encapsulant 116, for example, a sleeve 212 having the dimensions listed above. Then, optionally as indicated in phantom at 312 in FIG. 3, abrading the sheathing on the end of cable 124, again, for example, the polyethylene sheathing, and, optionally, cleaning 314 the abraded end of cable 124 to create a suitable surface to which an adhesive can adhere. The abrading step 312 may be practiced using a grinding tool or sandpaper, either manually or using an automated sander, for example, using #100 grit sandpaper. Cleaning step 314 may be practiced using isopropyl alcohol or another cleaning agent. After cleaning step 314, in one aspect of the invention, a priming step 315 may be performed. In the priming step 314, the surface of sheath 11 or the inside surface of sleeve 212, or both are treated to enhance bonding when the adhesive is applied in step 316. One primer that may be used is A43 Primer provided by Reltek. (Note that abrading 312, cleaning 314, and priming 315 may be omitted if the surface of the sheath is provided in a condition ready for an adhesive.)

Next, applying an adhesive 316, for example, Reltek's BONDiT™ B-45TH epoxy resin, to the outer surface of sheath 211, for example, in a thin layer over the outer surface of sheath 211. Then, inserting the sleeve 318 over the end of cable 124 having exposed conductor 210, for example, wherein conductor 210 passes through hole 206 in sleeve 212. Inserting step 318 may be practiced by a installing sleeve 212 over center conductor 210 and around the circumference of sheath 211 of cable 124 using a rotational motion so as to smooth out the layer of adhesive 214 and thereby minimizing the formation of air bubbles between sheath 211 and sleeve 212.

The next step is curing the adhesive 322 for a time at temperature (for example, as specified by the adhesive manufacturer). In curing step 322, curing may be practiced by means of a broad range of curing regimens, depending upon the adhesive used, the dimensions of the application, and the materials being bonded, among other things. For example, for curing a bond between a polyethylene-based sheath 211 and a silicone-based sleeve 212 using Reltek's BONDiT™ B-45TH epoxy resin at ambient temperature (that is, at about 60–80 degrees F, typically about 70 degrees F), the adhesive sets in about 4 hours, is tack free in about 12 hours, and is about 95% cured in about 24 hours. In addition, curing may be performed at elevated temperature. For example, in a two-part cure and post-cure regimen, again using Reltek BONDiT™ B-45TH epoxy resin, adhesive 214 is first cured for about 2 hours at ambient temperature to allow bubbles to escape, and then cured at about 150 degrees F. for about 4 hours to obtain about a 98% cure and then at about 200 degrees F for about 2 hours to complete the curing process.

After curing step 322, cable 124 having the sleeve 212, is attached 324 to conductor plate 118. In this attaching step 324, center conductor 210 of cable 124 is secured to plate 118, for example, secured to blind hole 131 of conductor plate 118, using conventional bonding techniques, such as soldering, brazing, welding, adhesives, mechanical fasteners, or combinations of two or more thereof. One adhesive that may be used is Tiga Silver 901 electrically-conductive adhesive sold by Resin Technology of South Easton, Mass. Once cable 124 is attached to plate 118, in the next step 326, the cable 124, along with base assembly 117, and the device (such as, x-ray tube 110), are all encased in encapsulant 116, for example, encased in one of the silicone encapsulants described above. Encasing 326 may be practiced using standard vacuum-potting techniques. For example, in encasing step 326, x-ray tube 110, base assembly 117, and the end of high-voltage cable 124 may be inserted into a mold and the mold filled with silicone encapsulant 116, such as Dow Chemical's SYLGARD® 184 silicone elastomer, and then allowed to cure as necessary. The cured structure is then removed from the mold to provide a structure as shown in FIG. 1, that is, an assembly of components surrounded by encapsulant 116. In one aspect of the invention, encasing 326 may comprise encasing one or more of the components only partially with encapsulant 116, for example, the high-voltage device or the base assembly 117 may be only partially encased in encapsulant. For example, as shown in FIG. 1, base plate 122 of base assembly 117 may not encased in encapsulant 116.

According to one aspect of the present invention, sleeve 212 and uncured encapsulant 116 are compatible wherein during encasing 326 an integral bond is formed between the surface of sleeve 212 and uncured encapsulant 116. According to this aspect of the invention, the bonding between sleeve 212 and encapsulant 116 during encasing 326 provides an attachment for high-voltage cable 124 with the high-voltage device, for example, x-ray producing device 100, with little or no air gaps between cable 124 and cured encapsulant 116. That is, according to this aspect of the present invention, a more integral connection between a high-voltage cable and a high-voltage device is provided which can provide extended service life to both the cable and the device compared to prior art methods and devices.

According to one aspect of the invention, the electrical connection provided is a "permanent" connection, that is, an electrical connection which is not meant to be readily disconnected or removed during the normal the operating life of the component. However, in one aspect of the invention, the connection may be removed, for example, for servicing of the component or servicing of the connection, and reconnected to the component, if necessary.

While the invention has been particularly shown and described with reference to preferred embodiment, it will be understood by those skilled in the art that various changes in form and details may be made to the invention without departing from the spirit and scope of the invention described in the following claims.

What is claimed is:

1. An electrical connector for an electrical device, the device comprising a conducting element at least partially encased in a curable encapsulant contained within a container of the device, the electrical connector comprising:
    a cable having a conductor and a sheath surrounding the conductor, the sheath comprising a first material that is not bondable with the uncured encapsulant; and
    an insulating sleeve over the sheath, the sleeve comprising a second material that is bondable with the uncured encapsulant;
    wherein an outer surface of the sleeve and the encapsulant form an essentially air-tight connection between the sleeve and the encapsulant when the encapsulant is cured upon insertion of the connector into the encapsulant.

2. The electrical connector as recited in claim 1, wherein the electrical device comprises a high-voltage electrical device.

3. The electrical connector as recited in claim 2, wherein the sleeve comprises a cylindrical sleeve having an end cap having a through hole for passing the conductor through the end cap.

4. The electrical connector as recited in claim 1, wherein the sleeve is mounted to the sheath by means of an adhesive.

5. The electrical connector as recited in claim 4, wherein the adhesive comprises an epoxy resin.

6. The electrical connector as recited in claim 1, wherein the encapsulant comprises a silicone encapsulant.

7. The electrical connector as recited in claim 6, wherein the silicone encapsulant comprises a silicone elastomer encapsulant.

8. The electrical connector as recited in claim 6, wherein the second material comprises a silicone material.

9. The electrical connector as recited in claim 8, wherein the second material comprises a cured silicone encapsulant.

10. The electrical connector as recited in claim 1, wherein the first material comprises a dielectric material.

11. The electrical connector as recited in claim 10, wherein the first material comprises a polyethylene dielectric material.

12. The electrical connector as recited in claim 1, wherein the second material comprises a silicone material.

13. The electrical connector as recited in claim 1, wherein the device comprises one of an x-ray tube, an x-ray transformer, a high-voltage rectifier, and high voltage power supply, and a microwave generator.

14. The electrical connector as recited in claim 1, wherein the first material comprises a polyethylene dielectric; the second material comprises a cured silicone encapsulant; and the encapsulant comprises a silicone elastomeric encapsulant; and sleeve is mounted to the sheath by means of an epoxy resin.

15. An insulating sleeve for a cable for use in connecting the cable to a device, the device comprising a conducting element at least partially encased in a curable encapsulant contained within a container of the device, the cable comprising a conductor and a sheath surrounding the conductor, the sheath comprising a first material that is not bondable with the uncured encapsulant, the sleeve comprising a cylindrical tube comprising a second material that is bondable with the uncured encapsulant to provide an essentially air-tight connection between an outer surface of the sleeve and the encapsulant when the encapsulant is cured upon insertion of the connector into the encapsulant.

16. The sleeve as recited in claim 15, wherein the device comprises a high-voltage device.

17. The sleeve as recited in claim 16, wherein the high-voltage device comprises one of an x-ray tube, an x-ray transformer, a high-voltage rectifier, a high-voltage power supply and a microwave generator.

18. The sleeve as recited in claim 15, wherein the curable encapsulant comprises a silicone encapsulant.

19. The sleeve as recited in claim 15, wherein the second material comprises a cured encapsulant.

20. The sleeve as recited in claim 15, wherein the sheath comprises an outer diameter and the sleeve comprises a circular cylindrical tube having an inner diameter, wherein the inner diameter of the sleeve is about equal to the outer diameter of the sheath.

21. The sleeve as recited in claim 20, wherein the inner diameter of the sleeve comprises a diameter between about 0.20 inches and about 1.0 inch.

22. The sleeve as recited in claim 15, wherein the sleeve further comprises an end cap.

23. The sleeve as recited in claim 20, wherein the sleeve end cap comprises a hole through which the cable conductor can pass.

24. The sleeve as recited in claim 15, wherein the second material bonds with the encapsulant without the use of adhesives.

25. A method for fabricating an electrical connection for a device, the device comprising a conducting element at least partially encased in a curable encapsulant contained within a container of the device, the method comprising:

providing a cable having a conductor and a sheath surrounding the conductor, the sheath having an outside surface having an outside diameter and comprising a first material that is not bondable with the uncured encapsulant;

providing a cylindrical insulating sleeve having an inside diameter about equal to the outside diameter of the sheath and comprising a second material that is bondable with the uncured encapsulant;

applying the sleeve over the sheath to provide a sleeved cable;

attaching the conductor of the sleeved cable to the conducting element of the device; and inserting the connector into the encapsulant thereby at least partially encasing the conducting element and the sleeved cable in the encapsulant wherein an outer surface of the sleeve and encapsulant bond to provide an essentially air tight connection between the sleeve and the encapsulant.

26. The method as recited in claim 25, wherein the device comprises a high-voltage device.

27. The method as recited in claim 25, wherein said applying comprises abrading the outside surface of the sheath.

28. The method as recited in claim 25, wherein said applying comprises applying an adhesive to the outside surface of the sheath.

29. The method as recited in claim 28, wherein said applying an adhesive to the outside surface of the sheath comprises applying an epoxy resin to the outside surface of the sheath.

30. The method as recited in claim 29, wherein said applying an adhesive comprises curing the adhesive for at least about 4 hours at about 70 degrees F.

31. The method as recited in claim 25, further comprising cleaning the outside surface of the sheath.

32. The method as recited in claim 31, wherein said cleaning the outside surface of the sheath comprises cleaning the outside surface of the sheath using alcohol.

33. The method as recited in claim 25, wherein attaching the conductor of the sleeved cable to the conducting element comprises one of soldering, brazing, and welding the conductor to the conducting element.

34. The method as recited in claim 25, wherein at least partially encasing the conducting element and the sleeved cable in an encapsulant comprises at least partially encasing the conducting element and the sleeved cable in a potting material.

35. The method as recited in claim 34, wherein the potting material comprises a silicone potting material.

* * * * *